United States Patent

Schwan et al.

[11] 4,014,886
[45] Mar. 29, 1977

[54] 2-SUBSTITUTED-5,6-DIMETHOXYIN-DAZOLES

[75] Inventors: Thomas J. Schwan; Charles S. Davis, both of Norwich; LeRoy J. Honkomp, Oxford, all of N.Y.

[73] Assignee: Morton-Norwich Products, Inc., Norwich, N.Y.

[22] Filed: Feb. 25, 1976

[21] Appl. No.: 661,392

Related U.S. Application Data

[62] Division of Ser. No. 472,719, May 23, 1974, Pat. No. 3,966,760.

[52] U.S. Cl. .......................... 260/293.6; 260/296 B
[51] Int. Cl.² ........................................ C07D 401/04
[58] Field of Search ...................... 260/293.6, 296 B

[56] References Cited
UNITED STATES PATENTS

| | | | |
|---|---|---|---|
| 3,152,135 | 10/1964 | Shavel et al. | 260/310 C |
| 3,736,332 | 5/1973 | Butula | 260/310 R |
| 3,821,180 | 6/1974 | Minieri et al. | 260/89.1 |

*Primary Examiner*—G. Thomas Todd
*Attorney, Agent, or Firm*—Anthony J. Franze

[57] ABSTRACT

Novel 2-substituted-5,6-dimethoxyindazoles of the formula:

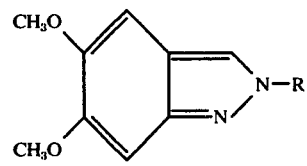

where R is cyclohexyl, phenethyl, phenyl, dimethylamino, aminoalkyl, methoxyethyl, indazolylethyl, tetrahydropyranylmethyl, p-dimethylaminophenyl, 2-hydroxyethyl, allyl, thiazolyl, pyridyl, 2,3-dihydroxypropyl, and hydroxy are useful as central nervous system depressants or hypotensive agents.

2 Claims, No Drawings

2-SUBSTITUTED-5,6-DIMETHOXYINDAZOLES

This is a division of application Ser. No. 472,719, filed May 23, 1974, now U.S. Pat. No. 3,966,760.

This invention relates to chemical compounds. More particularly it is concerned with a new series of compounds of the 2-substituted-5,6-dimethoxyindazole class represented by the formula:

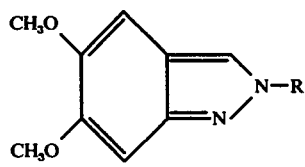

where R is cyclohexyl, phenethyl, phenyl dimethylamino, aminoalkyl, methoxyethyl, indazolylethyl, tetrahydropyranylmethyl, p-dimethylaminophenyl, 2-hydroxyethyl, allyl, thiazolyl, pyridyl, 2,3-dihydroxypropyl, and hydroxy.

The compounds of this invention possess pharmacological activity. Their pharmacological activity is evidenced in animals in depression of the central nervous system and/or by hypotensive activity. Thus, members of this series when dissolved or suspended in distilled water and administered intraperitoneally or orally to mice in doses ranging from 50–1600 mg/kg caused CNS depression characterized by dose related decreases in spontaneous motor activity, motor responsiveness to external stimuli, and in degree of excitability.

Hypotensive activity is exhibited by dose related decrease in arterial blood pressure when members of this series dissolved in distilled water were administered intravenously to anesthetized dogs at doses of 10–100 mg/kg.

Included in this invention is the compound 6-azidoveratraldehyde useful as an intermediate in the preparation of members of this series.

The compounds of this invention are readily prepared. Illustrative schema for the preparation thereof are depicted here below:

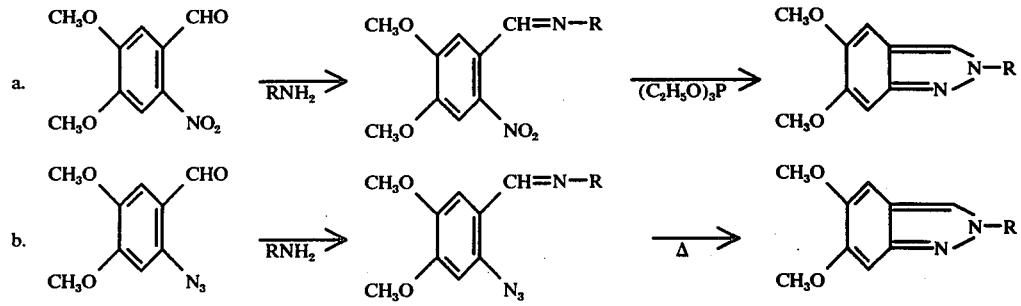

In these schema R is as above stated. The first step in scheme (a) is conducted in an inert solvent such as ethanol or toluene optionally catalyzed by glacial acetic acid. The cyclization is effected in refluxing triethyl phosphite. In scheme (b) the first step is conducted in an inert solvent such as dimethylformamide and ring closure is carried out in the same medium without isolation of the intermediate Schiff base.

The requisite azide for scheme (b) was synthesized as depicted below:

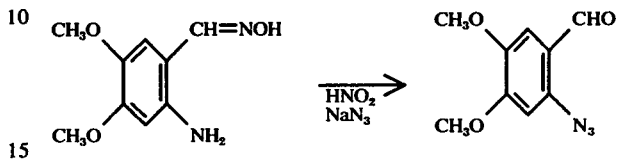

In this scheme the reaction is conducted in dilute hydrochloric acid with sodium azide affording an external source of azide ion.

2-Hydroxy-5,6-dimethoxyindazole can be readily prepared as depicted below:

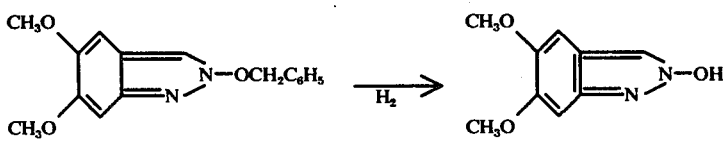

In this scheme the hydrogenolysis is conducted in the presence of palladium on carbon in a solvent such as ethanol.

In order that this invention may be readily available and understood by those skilled in the art, the following illustrative examples are appended.

EXAMPLE 1

A. 6-Nitroveratrylidenecyclohexylamine

A suspension of 42.2 g (0.2 mole) of 6-nitroveratraldehyde, 19.8 g (0.2 mole) cyclohexylamine, 1.0 ml. glacial acetic acid, and 1.25 l. ethanol was stirred and refluxed for 5 min., cooled, and filtered. The solid was washed with 100 ml. cold ethanol and air dried to give 47.0 g (80%) of the product, m.p. 160°–161°.

B. 2-Cyclohexyl-5,6-dimethoxyindazole

A suspension of 45 g (0.154 mole) of A and 63 ml. (60 g, 0.36 mole) triethylphosphite was refluxed in oil bath at 190°–200° for 4 hr. The phosphates and phosphites were removed in vacuo at 100°. The resulting mixture was cooled and the crystalline product was collected, washed with 100 ml. cold heptane, and air dried. The indazole, wt. 23 g (58%), m.p. 100°–103°, was combined with another 15 g of the product prepared by a similar method. Recrystallization of the combined product from 650 ml. boiling heptane gave 33 g of the product m.p. 102°–104.5°. Recrystallization from hexane gave the analytical sample, m.p. 102°–104°.

Anal. Calc'd for $C_{15}H_{20}N_2O_2$: C, 69.20; H, 7.74; N, 10.76. Found: C, 69.56; H, 7.76; N, 10.75.

EXAMPLE II

A. 6-Nitroveratrylidene-2-phenethylamine

To a heated suspension of 6-nitrovertraldehyde (84.4 g, 0.4 mole), ethanol (1000 ml), and 1 ml of glacial acetic acid was added to a solution of 2-phenethylamine (53.3 g, 0.44 mole) in 50 ml of ethanol. The resulting solution was refluxed for 1 hr and then cooled to precipitate 101 g (81%) of the product.

B. 2-(2-Phenethyl)-5,6-dimetoxyindazole

The product A (101 g, 0.3 mole) and triethylphosphite (137 ml, 0.74 mole) was refluxed for 4 hrs. The excess phosphite and phosphates were removed by vacuum distillation. The remaining black tar was dissolved in 300 ml of chloroform and extracted with three 150-ml portions of water. The chloroform extracts were dried over sodium sulfate and then concentrated to dryness. The crude indazole was recrystallized from heptane/ethyl acetate (2:1).

The analytical sample was recrystallized from heptane, m.p. 94°–96°. Calc'd. for $C_{17}H_{18}N_2O_2$: C, 72.32; H, 6.42; N, 9.92. Found: C, 72.40; H, 6.46; N, 10.14.

EXAMPLE III

A. 6-Nitroveratrylidene-N,N,-diethyl-p-phenylenediamine

To a refluxing, stirred suspension of 63.3 g (0.3 mole) of 6-nitroveratraldehyde and 1.0 ml glacial acetic acid in 800 ml ethanol was added over 15 min a solution containing 54 g (0.33 mole) of N,N-diethyl-p-phenylenediamine in 50 ml ethanol. The resulting solution was stirred and refluxed for 1 hr, then stored at 0°. The solid was collected, washed with 200 ml cold ethanol, and air dried to give 89 g (83%) of the product m.p. 117°–122°.

B. 2-(p-Diethylaminophenyl)-5,6-dimethoxyindazole dihydrochloride

A suspension of 88 g (0.247 mole) of A and 98 ml (94.6 g, 0.57 mole) of triethylphosphite was refluxed for 4 hr. The phosphate and phosphites were removed in vacuo. The residue was taken up in 300 ml chloroform and the solution was washed with four 200 ml portions of water, dried over magnesium sulfate, and concentrated to dryness in vacuo to give 94 g of the crude indazole. To a solution of the crude product in 1.5 l. hot methanol was added 250 ml methanolic hydrogen chloride. The solution was stored at 0° and there was deposited 53 g (54%) of the product, m.p. 225°–229°. Recrystallization from methanol gave 38 g of the dihydrochloride, m.p. 231°–234°. Further recrystallization from methanol gave the analytical sample, m.p. 233°–235°.

Anal. Calc'd. for $C_{19}H_{23}N_3O_2\cdot2HCl$: C, 57.29; H, 6.33; Cl, 17.80; N, 10.54. Found: C, 57.12; H, 6.34; Cl, 17.62; N, 10.61.

EXAMPLE IV

A. 6-Nitroveratrylidene-1,1-dimethylhydrazine

A heated suspension of 6-nitrovertraldehyde (84 g, 0.4 mole), ethanol (600 ml) and glacial acetic acid (1 ml) was treated with 1,1-dimethylhydrazine (26.4 g, 0.44 mole). The resulting solution was refluxed for 1 hr and cooled to give the product 83 g, m.p. 143°–145°.

B. 2-Dimethylamino-5,6-dimethoxyindazole hydrochloride

The product of A (83 g, 0.33 mole) was refluxed for 2.5 hrs with triethylphosphite (127 ml, 0.74 mole). The excess phosphite and phosphates were removed in vacuo and remaining residue was dissolved in 300 ml of chloroform. The chloroform solution was extracted with 3 × 150 ml of water and then dried over sodium sulfate. The chloroform was stripped leaving a dark viscous oil which solidified upon standing.

The free base was dissolved in dry ether and treated with methanolic hydrogen chloride to give 30 g of the product. Recrystallization from ethanol gave the analytical sample, m.p. 195°–196°.

Anal. Calc'd. for $C_{11}H_{15}N_3O_2\cdot HCl$: C, 51.26; H, 6.26; Cl, 13.76; N, 16.30. Found: C, 51.12; H, 6.12; Cl, 13.71; N, 1634.

EXAMPLE V

A. 6-Nitroveratrylidene-2-diethylaminoethylamine

To a stirring, refluxing suspension of 84.4 g (0.4) of 6-nitroveratraldehyde and 1.0 ml glacial acetic acid in 750 ml ethanol was added gradually a solution of 2-diethylaminoethylamine in 50 ml ethanol. The solution was refluxed and stirred for 1 hr; the solvents were then removed in vacuo. The residue was taken up in 300 ml chloroform; the solution was washed with three 150-ml portions of water, dried over magnesium sulfate, and concentrated to dryness in vacuo to give 123 g (100%) of the product.

B. 2-(2-Diethylaminoethyl)-5,6-dimethoxyindazole dehydrochloride

A solution of 37.6 g (0.12 mole) of A and 70 ml of 80% triethyl phosphite (54.4 g or 0.33 mole) was refluxed at 175° for 5 hr. The phosphites and phosphates were removed in vacuo. The residue was taken up in 380 ml 5% hydrochloric acid; the solution was washed with ether (4 × 150 ml), neutralized with 15% sodium hydroxide, and extracted with four 150 ml portions chloroform. The combined chloroform extracts were washed with 100 ml water, dried over magnesium sulfate, and concentrated to dryness in vacuo to give 25.5 g of the crude indazole. To a solution of the crude product in 100 ml methanol was added a solution of 30 g hydrogen chloride in 100 ml methanol. The solution was concentrated to dryness in vacuo to give 29 g of the crude hydrochloride. Recrystallization from ethanol give 12.5 g (30%) of the product, m.p. 194°–196°. The material was combined with 25.5 g of the material prepared in the same manner. The combined product was recrystallized from alcohol to give the analytical sample, m.p. 202°–204°.

Anal. Calc'd. for $C_{15}H_{23}N_3O_2\cdot HCl$: C, 51.43; H, 7.19; Cl, 20.26; N, 12.00. Found: C, 51.32; H, 7.28; Cl, 20.09; N, 11.88.

EXAMPLE VI

A.
6-Nitroveratrylidene-N-(γ-aminopropyl)morpholine

A solution of N-(γ:aminopropyl)morpholine (63 g, 0.44 mole) and ethanol (50 ml) was introduced to a heated suspension of 6-nitroveratraldehyde (84 g, 0.4 mole), ethanol (600 ml) and acetic acid (1 ml). The resulting solution was refluxed for 1.5 hrs and allowed to cool overnight. The solvent was stripped leaving a dark oil which was dissolved in chloroform (300 ml) and washed with water. The chloroform was stripped giving 127 g (95%) of the product.

B. 2-(3-Morpholinopropyl)-5,6-dimethoxyindazole dihydrochloride

The product A (127 g, 0.38 mole) was treated with triethylphosphite 144 g, 0.87 mole) and refluxed for 4.5 hrs. The excess phosphites and phosphates were removed under reduced pressure. The remaining dark oil was dissolved in chloroform (300 ml) and the solution washed with 3 × 150 ml of water. The chloroform solution was dried over sodium sulfate and then concentrated to give a dark oil.

The oil was dissolved in methanol (200 ml) and treated with methanolic hydrogen chloride. The recovered dihydrochloride (33 g, 22%) was washed with anhydrous ether and air dried.

The analytical sample m.p. 238°–239°, was recrystallized from methanol.

Anal. Calc'd. for $C_{16}H_{23}N_3O_3 \cdot 2HCl$: C, 50.80; H, 6.66; N, 11.11; Cl, 18.74. Found: C, 51.04; H, 6.85; N, 10.84; Cl, 18.38.

EXAMPLE VII

A.
6-Nitroveratrylidene-2-aminomethyltetrahydropyran

A solution of 2-aminomethyltetrahydropyran (51 g, 0.44 mole) and ethanol (50 ml) was slowly added to a heated suspension of 6-nitroveratraldehyde (84 g, 0.4 mole) and ethanol (600 ml). The resulting solution was refluxed for 1.5 hrs and cooled overnight. The solution was concentrated to dryness and the oil was dissolved in chloroform and washed with water. The chloroform extract was concentrated leaving a dark oil which crystallized upon standing. The solid was suspended in hexane and filtered (117 g, 95%), m.p. 89°–96°.

B.
5,6-Dimethoxy-2-(2-tetrahydropyranylmethyl)indazole

The product A (117 g, 0.38 mole) was treated with triethylphosphite (144 g, 0.87 mole) and refluxed for 2 hrs. The excess phosphite and phosphates were removed under reduced pressure. The remaining residue was dissolved in 300 ml of chloroform and the solution was washed with water (3 × 150 ml). The chloroform extract was dried over sodium sulfate and concentrated to dryness leaving a dark viscous oil. The oil was dissolved in benzene and passed through a column of aluminum oxide (2100 g). Elution with benzene gave 43 g of the product m.p. 90°–96°.

The analytical sample was recrystallized from heptane, m.p. 94.5°–96°.

Anal. Calc'd. for $C_{15}H_{20}N_2O_3$: C, 65.20; H, 7.30; N, 10.14. Found: C, 65.31; H, 7.08; N, 9.92.

EXAMPLE VIII

A. 1,2-Bis(6-Nitroveratrylidene)ethylenediamine

A heated suspension of 6-nitrovenatraldehyde (168.8 g 0.8 moles) and 1200 ml of ethanol was treated with ethylenediamine (24 g, 0.4 moles) and 200 ml of ethanol. The mixture was nearly in solution when a solid precipitated. Ethanol (500 ml) was added. The suspension was refluxed for 1.5 hrs. The resulting solid was filtered and washed with ethanol to yield 150 g (84%) of the product.

B. 1,2-Bis(5,6-Dimethoxy-2-indazolyl)ethane

The product A (150 g, 0.34 moles) was refluxed with triethylphosphite (279 g, 1.6 moles) for 4 hrs. The excess phosphites and phosphates were removed under reduced pressure leaving a dark semi solid. The material was dissolved in chloroform and washed with water (3 × 200 ml). The solution was dried over sodium sulfate and then concentrated to dryness to give the indazole. The material was recrystallized from isopropanol to yield a solid, m.p. 187°–190°.

The analytical sample, m.p. 194°–195°, was recrystallized from isopropanol.

Anal. Calc'd. for $C_{20}H_{22}N_4O_4$: C, 62.81; H, 5.80; N, 14.65. Found: C, 62.75; H, 5.89; N, 14.81.

EXAMPLE IX

A. 6-Nitroveratrylidene-2-methoxyethylamine

A suspension of 6-nitroveratraldehyde (84 g, 0.4 mole), 600 ml of ethanol, and 1 ml of acetic acid was refluxed with 2-methoxyethylamine (30 g, 0.44 mole) for 1.5 hrs. After cooling overnight filtration gave 78 g of the product; m.p. 65°–66°.

B. 2-(2-Methoxyethyl)-5,6-dimethoxyindazole hydrochloride

Product A (78 g, 0.33 mole) was treated with triethylphosphite (126 g, 0.76 mole) and refluxed 4 hrs. Phosphites and phosphates were removed under reduced pressure. The dark oil was dissolved in chloroform (300 ml) and thoroughly washed with water (3 × 150 ml). The chloroform extracts were dried over sodium sulfate and then concentrated to dryness. The indazole (115 g) was purified by dissolving in benzene and allowed to run through a column of aluminum oxide (20 g $Al_2O_2$/l g product). Elution with benzene gave 40 g of free base. The hydrochloride (28 g) was prepared by dissolving the free base in dry ether and treating with ethereal hydrogen chloride. The analytical sample was recrystallized from ethyl acetate, m.p. 159.5°–161°.

Anal. Calc'd. for $C_{12}H_{16}N_2O_3 \cdot HCl$: C, 52.84; H, 6.28; N, 10.27. Found: C, 53.08; H, 6.44; N, 10.37.

EXAMPLE X

A. 6-Nitroveratrylideneallylamine

A suspension of 6-nitroveratraldehyde (84 g, 0.4 mole) and ethanol (1200 ml) was refluxed with a solution of allylamine (21 g, 0.44 mole) and ethanol (100 ml) for 1.5 hrs. The resulting dark solution was concentrated to dryness in vacuo leaving 100 g of a dark oil which solidified.

B. 2-Allyl-5,6-dimethoxyindazole hydrochloride

The product A (148 g, 0.59 mole) was treated with triethylphosphite (226 g, 1.36 mole) and refluxed for 7.75 hrs. The excess phosphites and phosphates were removed under reduced pressure leaving a black oil. The oil was dissolved in chloroform (300 ml) and washed with water (3 × 150 ml). The chloroform extracts were combined and dried over sodium sulfate, then concentrated leaving a black oil. The oil was dissolved in benzene and passed through a column containing aluminum oxide (5 lb.) Elution with benzene followed by removal of the solvent left a light tan oil which was dissolved in ethyl ether and treated with ethereal hydrogen chloride. The resulting solid was recrystallized from isopropanol (hydrogen chloride saturated), to give 26 grams (25%) of the analytical sample, m.p. 174°–176°.

Anal. Calc'd. for $C_{12}H_{14}N_2O_2.HCl$: C, 56.58; H, 5.94; N, 11.00; Cl, 13.92. Found: C, 56.23; H, 6.08; N, 10.87; Cl, 13.69.

EXAMPLE XI

A. 6-Nitroveratrylidene-2-aminothiazole

To a heated solution of 6-nitroveratraldehyde (84 g, 0.4 mole) 500 ml of toluene, and 1 ml of acetic acid was added a suspension of 2-aminothiazole (50 g, 0.44 mole) and 250 ml of toluene. The material was refluxed until 7 ml of water was collected using a Dean-Stark apparatus. The solid was removed and the filtrate was concentrated leaving a light solid which was recrystallized from benzene to yield 84 g (71%) of the product, m.p. 125°–130°.

B. 2-(2-Thiazolyl)-5,6-dimethoxyindazole

The product A was treated with triethylphosphite (115 ml) and refluxed for 3 hrs. The phosphates and phosphites were removed under reduced pressure and the residue was dissolved in 300 ml of chloroform and washed with water (3 × 150 ml). The chloroform was dried over sodium sulfate and then concentrated leaving a dark oil. The oil was dissolved in benzene and slurried with aluminum oxide. The benzene was stripped leaving a light solid. The solid was recrystallized from ethanol to give the analytical sample, m.p. 184°–187°, wt. 10 g (9%).

Anal. Calc'd. for $C_{12}H_{11}N_3O_2S$: C, 55.16; H, 4.24; N, 16.08; S, 12.27. Found: C, 54.98; H, 4.64; N, 15.84; S, 11.84.

EXAMPLE XII

6-Azidoveratraldehyde

To hydrochloric acid (1287 ml), cooled to −10° with a dry ice-acetone bath, was added, in one portion, 6-aminoveratraldoxime (252 g. 1.3 moles). While maintaining at temperature 0° to −10° a solution of sodium nitrite (97.7 g, 1.4 mole) in water (412 ml) was added over ½ hr and the mixture was stirred for 30 minutes at 0° to −15°. The mixture was then treated with a solution of sodium azide (83.5 g, 1.3 mole) and water (386 ml) over ½ hr. The reaction mixture was then stirred for an additional 15 min. before diluting with water (3200 ml). With the temperature maintained below 0° the mixture was stirred for 1.5 hrs. The reaction mixture (below 0°) was then treated with aqueous sodium hydroxide (3470 ml, 25%). The mixture was stirred overnight at room temperature. The material was filtered, washed with water and dried to constant weight. Wt. product 207 g (77.7%), m.p. 112°–113.5°.

The analytical sample, m.p. 116°–118°, was obtained by recrystallization from isopropanol.

Anal. Calc'd. for $C_9H_9N_3O_3$: C, 52.17; H, 4.38; N, 20.28. Found: C, 52.12; H, 4.26; N, 20.29.

EXAMPLE XIII

2-Phenyl-5,6-dimethoxyindazole

A solution containing 51.8 g (0.25 mole) 6-azidoveratraldehyde (Example XII), 26.0 g (0.28 mole) aniline, 4 ml glacial acetic acid, and 300 ml dimethylformamide was stirred at 90°–100° for 1 hr, then refluxed for 1 hr until the gaseous evolution was complete. After the mixture was cooled and poured slowly in 1.5 l. iced water, the product was filtered, washed with two 150 ml portions cold water, and air dried to give 50 g of crude indazole, m.p. 130°–138°. Recrystallization from ethyl acetate - hexane followed by ethyl acetate gave 26 g (41%) of the product, m.p. 149°–152°. Recrystallization from ethyl acetate - hexane gave the analytical sample, m.p. 149°–152°.

Anal. Calc'd. for $C_{15}H_{14}N_2O_2$: C, 70.85; H, 5.55; N, 11.02. Found: C, 70.56; H, 5.51; N, 11.08.

EXAMPLE XIV

2-(2,6-Dimethylpiperidino)-5,6-dimethoxyindazole

A mixture of 6-azidovertraldehyde (Example XII) (62.1 g, 0.3 mole), 1-amino-2,6-dimethylpiperidine (38.4g, 0.3 mole), 3 ml acetic acid, and 300 ml dimethylformamide was heated at 100° for 4 hours and then refluxed for 60 min. The resulting solution was cooled to 50° and slowly poured into 2500 ml of iced water. The solids were then filtered, washed with water and air dried to give 55 g (63%) of the product.

The analytical sample was recrystallized from ethyl acetate, m.p. 162°–163°.

Anal. Calc'd. for $C_{16}H_{23}N_3O_2$: C, 66.41; H, 8.04; N, 14.52. Found: C, 66.42; H, 8.10; N, 14.41.

EXAMPLE XV

2-(3-Pyridyl)-5,6-dimethoxyindazole hydrochloride

A mixture of 6-azidoveratraldehyde (Example XII), (62 g, 0.3 moles),

A mixture of 6-azidoveratraldehyde (Example XII), (62 g, 0.3 moles), acetic acid (1 ml), dimethylformamide (250 ml) and 3-aminopyridine was heated at 90° for 3 hrs. The dark soln. was then refluxed for 1 hr and then allowed to stand overnight at room temperature. The dimethylformamide was stripped under vacuum and the remaining residue was poured into water (1500 ml). The aqueous solution was extracted with ethylacetate-(4 × 500 ml). The ethyl-acetate extract was dried over sodium sulfate and then concentrated to dryness. The resulting oil was dissolved in methanol, decolorized, and filtered. The methanolic filtrate was treated with methanolic hydrogen chloride to give 56 grams (64%) of product. The material was recrystallized from 2-ethoxyethanol (2500 ml) to yield 34 grams of the product, m.p. 230°–238°. The analytical sample, m.p. 243°–245°, was obtained by recrystallization from 2-ethoxyethanol.

Anal. Calc'd. for $C_{14}H_{13}N_3O_2.HCl$: C, 57.64; H, 4.64; N, 14.40. Found: C, 57.91; H, 4.93; N, 14.35.

EXAMPLE XVI

2-(2,3-Dihydroxypropyl)-5,6-dimethoxyindazole

A mixture of 6-azidovertraldehyde (Example XII) (83 g, 0.4 mole) and 1-amino-2,3-propanediol (37 g, 0.4 mole) was dissolved in dimethylformamide. The reaction mixture was treated with acetic acid (1.5 ml), heated at 90°–110° for 2 hrs and then refluxed until the evolution of nitrogen ceased (1 hr). The dimethylformamide was stripped under high vacuum to produce a black viscous tar. The tar was extracted with ethyl acetate (500 ml × 3), decolorized, and filtered. Upon standing a tan solid separated. Wt. product 30 g (30%), m.p. 113°–115°.

The analytical sample was recrystallized from ethyl acetate, m.p. 122°–124°.

Anal. Calc'd. for $C_{12}H_{16}N_2O_4$: C, 57.13; H, 6.39; N, 11.11. Found: C, 57.31; H, 6.44; N, 11.28.

EXAMPLE XVII

2-(3-Dimethylaminopropyl)-5,6-dimethoxyindazole dihydrochloride

A mixture of 6-azidovertraldehyde (Example XII) (72 g, 0.35 mole), dimethylformamide (250 ml), 3-dimethylaminopropylamine (40.8 g, 0.4 mole) and 1 ml of acetic acid was heated at 90°–110° for 2 hrs. The solution was then refluxed until nitrogen ceased to be evolved (1 hr). The dimethylformamide was removed under high vacuum leaving a dark oily substance. This material was dissolved in methanol, decolorized and filtered. The methanol was stripped leaving 101 g of dark oil. The oil was dissolved in methanol and treated with methanolic hydrogen chloride. The solvent was removed in vacuo and the residue was triturated with isopropanol to give 21 g of the product. The isopropanol filtrate was treated with isopropanolic hydrogen chloride to yield another 40 g of title compound. The two fractions were combined and recrystallized from methanol to give 35 g (29%) of the product.

The analytical sample, m.p. 228°–230°, was obtained by recrystallization from methanol.

Anal Calc'd. for $C_{14}H_{21}N_3O_2\cdot 2HCl$: C, 50.01; H, 6.89; N, 12.50; Cl, 21.09. Found: C, 49.76; H, 6.98; N, 12.31; Cl, 20.84.

EXAMPLE XVIII

2-(2-Hydroxyethyl)-5,6-dimethoxyindazole

A mixture of 6-azidovertraldehyde (Example XII) (62g, 0.3 mole), 2-aminoethanol (18.3 g, 0.3 mole), acetic acid (1 ml) and dimethylformamide (250 ml) was heated at 90°–110° for 1 hr. The resulting solution was refluxed for an additional 1 hr. The dimethylformamide was removed under high vacuum to give 58 g of crude indazole. The material was recrystallized from toluene (Darco) to yield 38 g (57%) of the product, m.p. 122°–124°.

The analytical sample was recrystallized twice from toluene, m.p. 125°–127°.

Anal. Calc'd. for $C_{11}H_{14}N_2O_3$: C, 59.45; H, 6.35; N, 12.61. Found: C, 59.36; H, 6.26; N, 12.57.

EXAMPLE XIX

A. O-Benzyl-6-nitroveratraldoxime

6-Nitroveratraldoxime (113 g, 0.5 mole) was dissolved in 2500 ml of dimethylformamide. To this solution was added sodium methoxide (27 g, 0.5 mole). The suspension was treated with benzyl chloride (63 g, 0.5 mole) and stirring was continued for an additional 4 hr. The orange suspension was diluted with 3 l. of water and the solid was filtered, m.p. 109°–113°, yield: 110 g (78%). A small amount of the material was recrystallized from toluene to give an analytical sample melting at 116°–117°.

Anal. Calc'd. for $C_{16}H_{16}N_2O_5$: C, 60.75; H, 5.10; N, 8.86. Found: C, 61.11; H, 5.04; N, 8.96.

B. 2-Benzyloxy-5,6-dimethoxyindazole

The product A (105 g, 0.33 mole) and triethyl phosphite (140 g, 0.8 mole) were heated together until the pot temperature reached 135° C. External heating was discontinued as the reaction became exothermic. The pot rose to a peak of 190° C. When the pot temperature dropped to 170° C, an additional 20 ml of triethyl phosphite was added. The pot temperature was maintained at 170° C for 4 hr and then cooled to room temperature. The dark mixture was placed in a refrigerator overnight. The solid was removed by filtration to give 80 g of crude indazole. The crude material was dissolved in 150 ml of boiling ethanol and hot water was added to the cloud point. The ethanol-water solution was slowly cooled to give plates melting at 123°–125° C. A small amount of crude material was recrystallized from benzene-hexane to give an analytical sample melting at 124°–125°.

Anal. Calc'd. for $C_{16}H_{16}N_2O_3$: C, 67.59; H, 5.67; N, 9.85. Found: C, 67.20; H, 5.58; N, 9.96.

C. 2-Hydroxy-5,6-dimethoxyindazole 14.2 g (0.05 mole) of product B was suspended in 250 ml of ethanol. 5 g of 5% Pd/C (50% moisture) was added to the suspension. The mixture was hydrogenated at 50 psi until the theoretical amount of hydrogenation was absorbed (ca. 5 min.).

The mixture was heated on the steam bath to boiling and then filtered. The filtrate was concentrated under vacuum to give a pink solid. The product was recrystallized from acetonitrile, m.p. 185°–186°, wt. 9 g (92%).

Anal. Calc'd. for $C_9H_{10}N_2O_3$: C, 55.67; H, 5.19; N, 14.43. Found: C, 55.70; H, 5.32; N, 14.24.

What is claimed is:

1. The compound 2-(2,6-dimethylpiperidino)-5,6-dimethoxyindazole.

2. The compound 2-(2-pyridyl)-5,6-dimethoxyindazole hydrochloride.

* * * * *